United States Patent [19]

Abe et al.

[11] Patent Number: 4,985,556

[45] Date of Patent: * Jan. 15, 1991

[54] PERFLUORO(DIALKYLAMINOPROPENE) DERIVATIVES

[75] Inventors: Takashi Abe, Kasugai; Eiji Hayashi, Konan, both of Japan

[73] Assignees: Agency of Industrial Science & Technology; Ministry of International Trade & Industry, both of Tokyo, Japan

[*] Notice: The portion of the term of this patent subsequent to Nov. 1, 2005 has been disclaimed.

[21] Appl. No.: 242,308

[22] Filed: Sep. 9, 1988

[30] Foreign Application Priority Data

| Sep. 10, 1987 | [JP] | Japan | 62-227467 |
| Sep. 10, 1987 | [JP] | Japan | 62-227468 |
| Sep. 10, 1987 | [JP] | Japan | 62-227469 |
| Sep. 10, 1987 | [JP] | Japan | 62-227470 |

[51] Int. Cl.$^5$ .................. C07C 87/26; C07D 207/00; C07D 211/00; C07D 241/04
[52] U.S. Cl. .................. 540/484; 540/610; 544/106; 544/175; 544/358; 544/399; 546/184; 546/248; 548/400; 548/571; 562/849; 562/852; 564/468; 564/509; 564/510
[58] Field of Search .................. 260/544 F, 543.2; 540/484, 610; 544/106, 175, 399, 358; 548/400, 571; 564/510, 509; 546/248; 562/849

[56] References Cited

U.S. PATENT DOCUMENTS

| 3,311,599 | 3/1967 | Fawcett | 526/248 |
| 3,471,484 | 10/1969 | Guenthner | 544/175 |
| 4,782,148 | 11/1988 | Abe et al. | 540/484 |
| 4,912,216 | 3/1990 | Abe | 540/484 |

FOREIGN PATENT DOCUMENTS 62-22756 1/1987 Japan .

OTHER PUBLICATIONS

Banks et al., Journal of Chemical Society, Perkin I, p. 5, (1973).
Banks et al., Journal of Chemical Society (c), p. 2608, (1968).
Chemical Abstract vol. 83 (1975):192468s, Fleming et al.
Chem. Abstract vol. 93 (1980):185663e, Vinogradov et al.
Journal of Chemical Society, Perkin I pp. 1633-1638, 1975, G. L. Fleming, et al.

Primary Examiner—Mukund J. Shah
Assistant Examiner—Philip Datlow
Attorney, Agent, or Firm—Oblon, Spivak, McClelland, Maier & Neustadt

[57] ABSTRACT

Perfluorocarboxylic acid fluorides represented by the formula A-B, wherein A is either

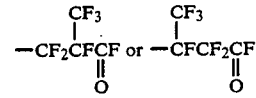

and B stands for a perfluoro-di-substituted amino group, and perfluoro(dialkylaminopropenes) represented by the formula A″-B″, wherein A″ stands for

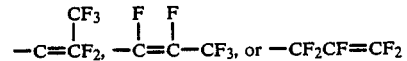

and B″ has the same meaning as B defined above, are novel compounds. Methods for the production of these novel compounds are also disclosed.

12 Claims, No Drawings

PERFLUORO(DIALKYLAMINOPROPENE) DERIVATIVES

BACKGROUND OF THE INVENTION

1. Field of the Invention

This invention relates to novel perfluorocarboxylic acid fluorides, nitrogen-containing perfluoropropenes, and a method for the production of these compounds. More particularly, this invention relates to perfluoro(-dialkylaminobutyryl fluorides) and perfluoro(dialkylaminopropenes) which are useful intermediates for the manufacture of fluorine-containing products such as surfactants, agricultural pesticides, and medicines and for the synthesis of fluorine-containing macromolecular monomers and to a method for efficient production of these compounds from readily available raw materials.

2. Prior Art Statement

In recent years, fluorine-containing compounds of various kinds have been developed. For example, perfluorocarboxylic acid fluorides such as perfluorocaprylyl fluoride and olefin compounds such as perfluoroolefins containing a perfluoro(N,N-dialkyl)amino group (described more fully later) have found extensive utility as intermediates for the synthesis of surfactants, dyes, agricultural pesticides, and medicines and as monomers for the manufacture of fluorine-containing macromolecular compounds, for example.

The perfluorocarboxylic acid fluorides mentioned above have been heretofore produced mainly by the electrolytic fluorination method. Beside this method, a method employing the reaction of $R_fI$ with $SO_3$ or with $ClSO_3H$ (French Pat. No. 1,343,661 and U.S. Pat. No. 3,238,240) and a method employing the oxidation of $R_fCH=CCl_2$ (Japanese Patent Public Disclosure SHO 60(1985)-188345) (wherein $R_f$ stands for a perfluoroalkyl group) are known to the art.

The only perfluorocarboxylic acid fluorides containing a nitrogen atom as a hetero atom known to the art are, perfluoro(N,N-dimethylaminoacetyl fluoride) ["Journal of American Chemical Society", vol. 80, page 1,889 (1959)], perfluoro ($\beta$-alkylaminopropionyl fluorides) (U.S. Pat. No. 3,471,484), and perfluoro($\alpha$-alkylaminopropionyl fluorides) (Japanese Patent Applications SHO 60(1985)-103042 and SHO 60(1985)-166,888). No other long-chain carboxylic acid fluoride containing a perfluorodialkylamino group are known to exist.

Fluorine-containing olefin compounds will now be described. For example, perfluoroolefins containing a perfluoro(N,N-dialkyl)amino group possess a double bond as a portion for reaction. By using these compounds as an intermediate raw material, therefore, various useful compounds possessing the perfluoro(N,N-dialkylamino) group can be produced. When these perfluoroolefins are copolymerized with other fluoroolefins to effect incorporation of the perfluoro(N,N-dialkylamino) group in the products of the copolymerization, the produced copolymers enjoy improvements in crystallinity and mechanical properties.

As the perfluoroolefins described above, perfluoro(N-vinylamines) such as perfluoro(N,N-dimethylvinylamines) (U.S. Pat. No. 3,311,599), perfluoro(N-vinylpyrrolidines) (Japanese Patent JP 62-22755(1987)), perfluoro(N-vinylmorpholines) ["Journal of Chemical Society", Perkin I, page 5 (1973)], and perfluoro(N-vinylpiperidine) ["Journal of Chemical Society", (C) page 2,608 (1968)] and perfluoro[3-(N,N-dimethylamino)-2-propene] ["Journal of Chemical Society", Perkin I, page 1,633 (1975)] are currently known. Among these perfluoroolefins, perfluoro[3-(N,N-dimethylamino)-2-propene], which is the only known perfluoro[(N,N-dialkyl)propenylamine], is synthesized by a two-step reaction methodologically, i.e. (1) first causing radical addition reaction of N-bromobistrifluoromethylamine with 1H-pentafluoropropene-1 thereby obtaining a 1:1 adduct and (2) then subjecting the 1:1 adduct to a dehydrogen bromide reaction thereby forming an unsaturated bond in the reaction product.

To be specific, the two-step reaction is represented by reaction formulas as follows.

(1) First step:

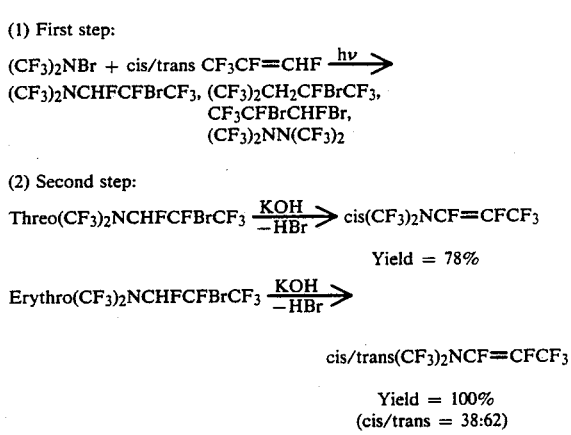

(2) Second step:

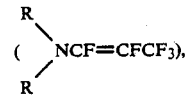

Yield = 78%

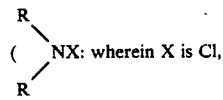

cis/trans$(CF_3)_2NCF=CFCF_3$

Yield = 100%
(cis/trans = 38:62)

This method, however, has an inherent defect in that it is incapable of synthesizing $(CF_3)_2NCF_2CF=CF_2$ as a terminal olefin. Further, the synthesis of $(CF_3)_2NBr$ and $CH_3CF_2=CHF$ as raw materials requires many complicated treatment steps. Since this method necessitates the two-step key reaction mentioned above, it has another disadvantage in that it is complicated operationally. When this method is applied to the synthesis of another kind of perfluoroalkenylamine, $$\begin{array}{c} R \\ ( \quad \diagdown \\ \quad \quad NCF=CFCF_3), \\ ( \quad \diagup \\ R \end{array}$$

the synthesis of a perfluoroalkylamino radical donor, $$\begin{array}{c} R \\ ( \quad \diagdown \\ \quad \quad NX: \text{ wherein X is Cl}, \\ ( \quad \diagup \\ R \end{array}$$

wherein X is Cl, Br, or F), indispensable to the synthesis of the 1:1 adduct as a precursor, is difficult. Thus, this method has a disadvantage in that it cannot be easily utilized for general purposes.

OBJECT AND SUMMARY OF THE INVENTION

An object of this invention is to provide novel perfluorocarboxylic acid fluorides and novel nitrogen-containing perfluoropropenes useful as intermediates for synthesis and a method for the production of these compounds from readily available raw materials.

The inventors continued a study with a view to accomplish the object described above. They consequently found that reactive derivatives of 3-dialkylamino-iso-butyric acid or 3-dialkylamino-n-butyric acid are readily available, that when these compounds are electrolytically fluorinated in liquid hydrogen fluoride, novel corresponding perfluoro(3-dialkylamino-iso-butyryl fluoride) or corresponding perfluoro(3-alkylamino-n-butyryl fluoride) is obtained in a relatively desirable yield without readily inducing a reaction of cyclization as a secondary reaction or any appreciable cleavage of the C—N bond, and that, unexpectedly, a novel perfluoro(dialkylaminopropene) is obtained by using a fluoride or salt of perfluoro(iso-butyric acid) or perfluoro(n-butyric acid) each possessing a perfluoro(N,N-dialkylamino) group at the 3 position as a raw material and subjecting this raw material to a heat treatment at a specific temperature. This invention has been perfected on the basis of this finding.

To be specific, this invention is directed to a perfluoro-carboxylic acid fluoride represented by the formula A-B, wherein A stands for one member selected from the group consisting of

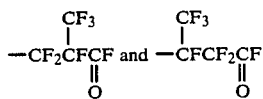

and B for a perfluoro-di-substituted amino group having a total of 2 to 6 backbone carbon atoms, to a method for the production of the fluoride mentioned above characterized by electrolyzing in a liquid hydrogen fluoride an ester or other reactive derivative of 3-dialkylaminocarboxylic acid represented by the formula A'-B', wherein A' stands for one member selected from the group consisting of

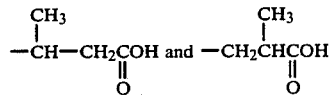

and B' for a di-substituted amino group substituted with an alkyl having a total of 2 to 6 backbone carbon atoms, to a perfluoro(dialkylaminopropene) represented by the formula A"-B", wherein A" stands for one member selected from the group consisting of

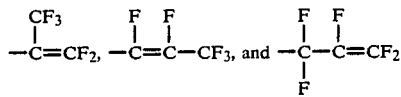

and B" for a perfluoro-di-substituted amino group substituted with a perfluoroalkyl group having a total of 4 to 6 backbone carbon atoms where A" stands for

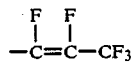

or a perfluoro-di-substituted amino group substituted with a perfluoroalkyl group having a total of 2 to 6 backbone carbon atoms where A" stands for

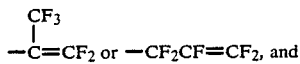

to a method for the production the perfluoro(dialkylaminopropene) mentioned above characterized by heating at a temperature in the range of 100° to 500° C. a perfluorocarboxylic acid derivative represented by the formula A'''-B''', wherein A''' stands for one member selected from the group consisting of

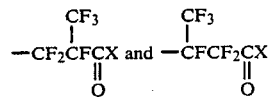

(wherein X stands for a fluorine atom, a perfluoroalkoxy group, or an OM group, providing that M stands for a monovalent alkali metal or alkaline earth metal) and B" for a perfluoro-di-substituted amino group having a total of 2 to 6 backbone carbon atoms.

DETAILED DESCRIPTION OF THE PREFERRED EMBODIMENTS

First, the perfluorocarboxylic acid fluoride of the present invention will be described below.

The perfluoro-di-substituted amino group, B having a total of 2 to 6 backbone carbon atoms can be represented by the formula,

In this formula, $R_1$ and $R_2$ independently stand for a perfluoroalkyl group having 1 to 5 carbon atoms. The two groups may be bonded directly to each other or indirectly through the medium of an oxygen atom or a nitrogen atom. Together with the nitrogen atom to which they are bonded, they may form a five-membered, six-membered, or seven-membered heterocyclic ring.

The dialkyl-substituted amino group, B', having a total of 2 to 6 backbone carbon atoms and used as a raw material for the perfluorocarboxylic acid fluoride can be represented by the formula,

In this formula, $R_1'$ and $R_2'$ independently stand for an alkyl group of 1 to 5 carbon atoms. These two groups may be bonded directly to each other or indirectly through the medium of an oxygen atom or a nitrogen atom. Together with the nitrogen atom to which they are bonded, they may form a five-membered, six-membered, or seven-membered ring.

Specifically, the perfluorocarboxylic acid fluoride of this invention is represented by the following formula:

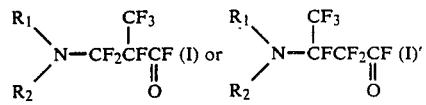

and is produced by electrolyzing in liquid hydrogen fluoride a reactive derivative of the formula:

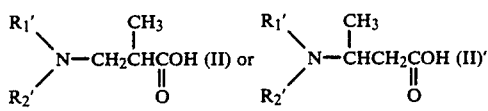

The perfluoro(3-dialkylamino-iso-butyryl fluorides) and the perfluoro(3-dialkylamino-n-butyryl fluorides) represented by the formulas (I) and (I)' are all novel compounds not reported in the literature to date.

Concrete examples of the fluorination of (II) or (II)' into (I) or (I)', i.e. the conversion of

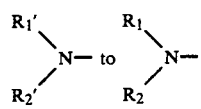

are shown below.

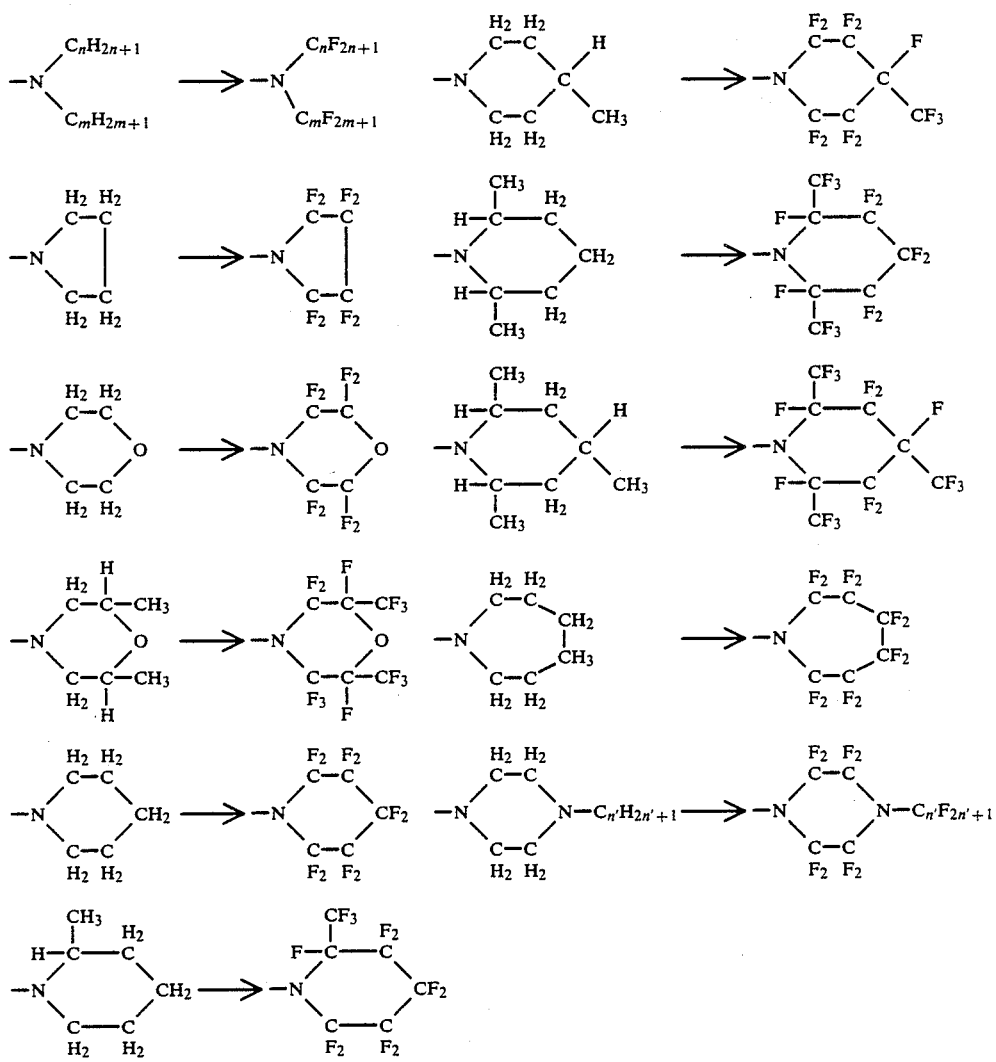

(wherein n, n', and m independently stand for an integer in the range of 1 to 5, provided that n+m falls in the range of 2 to 6).

In the present invention, as raw materials for the perfluoro(3-dialkylamino-iso-butyryl fluorides) and perfluoro(3-dialkylamino-n-butyryl fluorides) represented by the general formulas (I) and (I)', reactive derivatives of 3-dialkylamino-iso-butyric acid and 3-dialkyl-amino-n-butyric acid represented by the general formulas (II) and (II)' are respectively used. Acid halides, lower alkyl esters, acid anhydrides, and unsubstituted or N-mono-, di-alkyl-substituted acid amides can be cited as concrete examples of the reactive derivatives.

In these reactive derivatives, 3-(N,N-dialkylamino)-iso-butyric acid methyl esters and 3-(N,N-dialkylamino)-n-butyric acid methyl esters prove to be particularly desirable because they are readily available and because they produce tarry products only sparingly during the course of electrolysis. They can be obtained easily and inexpensively by Michael reaction in high yield, for example, by the method proposed by Perring ["Journal of Organic Chemistry", vol. 18, page 901 (1933)], specifically by subjecting corresponding secondary amines and methyl methacrylate or methyl crotonate to an addition reaction.

For the electrolytic fluorination reaction of this invention, the electrolytic cell commonly used in the conventional electrolytic fluorination reaction can be used. This reaction is carried out in liquid hydrogen fluoride. The concentration of the reactive derivative of 3-dialkylaminobutyric acid as a raw material in the liquid hydrogen fluoride is selected generally in the range of 1 to 80% by weight, preferably 3 to 20% by weight, because the reaction itself lacks practicality if the concentration is unduly low and the production of tarry substance is conspicuous if the concentration is unduly high. The current density is selected generally in the range of 0.01 to 10 A/dm², preferably 0.1 to 5 A/dm². If the current density is unduly high, the electrolytic voltage is so high as to encourage occurrence of secondary reactions. The electrolytic temperature is selected generally in the range of −20° to 50° C., preferably −10° to 20° C. If the electrolytic temperature is unduly low, the electrolytic pressure increases excessively. Conversely, if it is unduly high, the diffusion of hydrogen fluoride occurs readily.

Though this electrolytic reaction is generally carried out under normal pressure, it may be performed under application of pressure as occasion demands. The electrolytic reaction performed under application of pressure has an advantage in that the boiling point of hydrogen fluoride is increased and, therefore, the cooling of the reaction system can be alleviated. The reaction can be carried out as effectively in a continuous manner as batchwise. In batchwise operation, the electrolytic time required for completion of the reaction depends on the magnitude of current density and the amount of raw material. Generally, the time spent for this reaction is desired to be such that the actual amount of electric power reaches a level falling in the range of 80 to 200% of the theoretical amount.

These conditions for the electrolytic fluorination are variable with the kind of raw materials to be used. Thus, they are desired to be selected suitably with consideration to the yield of the product aimed at, the current efficiency, etc. For the electrolytic fluorination to proceed efficiently and the product aimed at to be obtained in high yields, the electrolyte is desired to be kept stirred during the course of the reaction. This stirring may be attained by subjecting the electrolyte to forced mechanical agitation or by introducing a continued flow of inert gas into the electrolyte, for example.

When perfluoro(3-dialkylamino-iso-butyryl fluoride) and perfluoro(3-dialkylamino-n-butyryl fluoride) obtained as described above have relatively low boiling temperatures (about 40° to 100° C.), they may possibly depart from the electrolytic cell in conjunction with the gas formed in the course of the electrolysis. In this case, the products aimed at may be collected by passing the formed gas entraining the products through a bed of pellets of sodium fluoride, for example, thereby separating hydrogen fluoride and then passing the gas through a cooling trap. When the perfluoro(3-dialkylamino-iso-butyryl fluoride) and the perfluoro(3-dialkylamino-n-butyryl fluoride) have high boiling temperatures (at least about 100° C.), they mostly remain in the electrolytic cell resist solution in the liquid hydrogen fluoride and constitute one of two clearly separated layers, the other being a hydrogen fluoride layer. Thus, they can be collected after completion of the electrolysis by means of draining.

By the electrolytic fluorination reaction described above, perfluoro(3-dialkylamino-iso-butyryl fluoride) or perfluoro(3-dialkylamino-n-butyryl fluoride) represented by the general formula (I) can be obtained from the corresponding reactive derivatives of 3-dialkylamino-iso-butyric acids or 3-dialkylamino-n-butyric acid represented by the general formula (II).

Now, the perfluoro(dialkylaminopropenes) contemplated by the present invention will be described below.

The perfluoro-di-substituted amino group, B″, having a total of 2 to 6 backbone carbon atoms and contained in the perfluoro(dialkyl-aminopropenes) and in the perfluorocarboxylic acid derivatives as raw materials therefor is identical with the aforementioned B and may be represented as

The perfluoro(dialkylaminopropenes) of the present invention fall under the three kinds, represented by the formulas,

 (III)

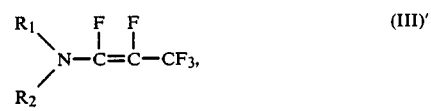 (III)' and

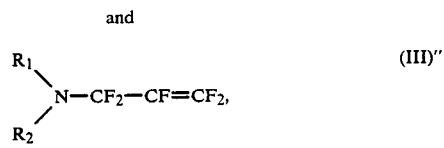 (III)'' and those of the kind (III) are produced by heating

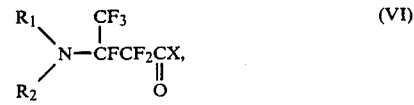 (VI)

and those of the kinds (III), and (III)'' by heating

 (VI)' respectively at a temperature in the range of 100° to 500° C.

In these formulas, X stands for a fluorine atom or an OM group (provided that M stands for an alkali metal or an alkaline earth metal equivalent to the valency of one) and

for entirety the same perfluorocarboxylic acid fluoride as presented by the formula (I) or (I)'.

The perfluoro-3-dialkylamino-iso-butyric acid derivative and perfluoro-3-dialkylamino-n-butyric acid derivative represented by the formulas (VI) and (VI') can be easily produced as described above by subjecting 3-dialkylamino-substituted butyric acid and reactive derivatives thereof such as, for example, acid halides and esters represented by the formulas,

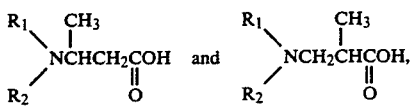

to electrolytic fluorination in liquid hydrogen fluoride.

The products of this electrolytic fluorination can be converted into corresponding salts by causing them to be reacted upon by the hydroxide of an alkali metal or an alkaline earth metal.

The propene compounds represented by the aforementioned formulas (III), (III)', and (III)" can be easily produced by simply heating the compounds represented by the formula (VI) and (V)' at a temperature in the range of 100° to 500° C. For the purpose of facilitating thermal decomposition of a reaction system, preferred raw materials for the production of the propene compounds (III) are perfluoro(3-dialkylamino-n-butyryl fluoride), sodium and potassium salts of perfluoro(3-dialkylamino-n-butyric acid), and those for the production of the propene compound of (III)' and (III)" are perfluoro(3-di-alkylamino-iso-butyryl fluoride), sodium and potassium salts of perfluoro(3-dialkylamino-iso-butyric acid).

The temperature for the thermal decomposition is required to be selected in the range of 100° to 500° C., preferably 200° to 300° C. If this temperature is lower than 100° C., the conversion to be attained is too low for the reaction to be practical. If the temperature exceeds 500° C., the reaction tends to entail secondary reactions such as undesirable decomposition. Though the reaction time depends on the temperature of treatment, it generally is in the range of 10 seconds to two hours. The reaction time decreases in proportion as the temperature of treatment increases, whereas the reaction time increases in proportion as the temperature of treatment decreases. Thus, these reaction conditions are desired to be selected suitably.

The reaction pressure is not a significant factor in this reaction of thermal decomposition. Therefore, the reaction can be carried out equally effectively under a vacuum, under normal pressure, or under application of pressure. It is desired to be carried out either under normal pressure or under a vacuum, however, because the recovery of the reaction product is effected more easily than under application of pressure. In the reaction of thermal decomposition, an inert gas such as nitrogen, helium, argon, or carbon dioxide or an aprotic liquid compound such as a polyether, tetrachloroethylene, or n-heptane can be used as a diluent, depending on the particular form of reaction to be used. In this case, the ratio of dilution is desired not to exceed 100 times the original amount.

When a perfluoro(3-dialkylamino-n-butyryl fluoride) or a perfluoro(3-dialkylamino-iso-butyryl fluoride) is used as a raw material in the method of this invention, the reaction of thermal decomposition is desired to be carried out in the presence of a metal salt or a metal oxide. In this case, the product aimed at can be easily obtained when the reaction of thermal decomposition is carried out by continuously supplying the raw material to a packed bed of the metal salt or metal oxide kept at a prescribed temperature.

In this invention there is no particular limitation on the material of the reaction vessel for the thermal decomposition but a reaction vessel made of stainless steel or Hastelloy is generally used. The form of the packed bed mentioned above is not particularly restricted but may be in any of the conventional forms such as, for example, a fixed bed, a moving bed, or a fluidized bed.

Concrete examples of the metal salt include sodium carbonate, potassium carbonate, lithium carbonate, sodium phosphate, potassium phosphate, barium carbonate, calcium carbonate, magnesium carbonate, potassium sulfate, and sodium sulfate. Concrete examples of the metal oxide include zinc oxide and cadmium oxide. Among the metal compounds enumerated above, such solid bases as sodium carbonate and potassium carbonate prove to be particularly desirable on account of their ability to decompose the noxious $COF_2$ which is liberated by the reaction of thermal decomposition.

By the present invention, the novel compounds aimed at, i.e. the perfluoro(3-dialkylamino-iso-butyryl fluoride), perfluoro(3-dialkylamino-n-butyryl fluoride), perfluoro(2-dialkylaminopropenes), and perfluoro(3-dialkylaminopropenes) are produced very easily from readily available raw materials. These products have very high commercial value as intermediates and macromolecular monomers for the synthesis of such fluorine-containing products as surfactants, agricultural pesticides, and medicines.

Now, the present invention will be described more specifically below with reference to working examples. It should be noted, however, that this invention is not restricted in any sense by these examples.

An electrolytic cell was used in all the experiments described in Examples 1 to 12. This electrolytic cell was made of Monel metal and was provided with seven anodes of nickel plate and eight cathodes alternately disposed as spaced at a fixed interval of 2 mm, the anodes each having an available surface area of 7.5 $dm^2$.

EXAMPLE 1

In the electrolytic cell, 450 ml of anhydrous hydrofluoric acid was placed and subjected to preliminary electrolysis for removal of trace impurities entrained thereby. Then, the product of the preliminary electrolysis and 44.9 g of methyl 3-dimethylamino-iso-butyrate added thereto were subjected to 316 A.hr electrolysis under the conditions of an anode current density of 3.3 $A/dm^2$, bath temperature of 7° to 9° C., and electrolytic voltage of 5.9 to 6.1 V.

The gas produced consequently was passed through a tube filled with sodium fluoride to expel the hydrogen fluoride entrained by the gas after passing through a reflux condenser kept at −25° C., and then collected in a trap cooled to −78° C. As a result, 32.7 g of a fluorocarbon mixture was obtained. After the electrolysis, the cock at the lower end of the electrolytic cell was opened to remove 20.7 g of high boiling fluorocarbons as a cell drain compound. These products were treated with a small amount of pellets of Molecular Sieve 4A to remove a trace of hydrogen fluoride still remaining therein and subsequently analyzed by gas chromatography [carrier: He, liquid phase: 1,6-bis(1,1,12-trihydroperfluorododecyloxy)hexane, carrier: Chromosorb PAW], IR, $^{19}F$ NMR, Mass, and elementary analysis (for carbon). It was found that the treatment produced 31.3 g of perfluoro(3-dimethylamino-iso-butyryl fluoride) (yield 28.9 mol %; mol % will be expressed simply as % hereinafter). At the same time, the treatment simultaneously produced perfluoro(iso-butyryl fluoride)

and perfluoro(N,N-dimethyl-n-propylamine) as cleavage compounds.

The perfluoro(3-dimethylamino-iso-butyryl fluoride) is a novel compound, possessing a boiling point of 60.5° to 61.5° C. and a $d_4^{20}$ value of 1.7120 and exhibiting in the infrared absorption spectrum thereof characteristic absorptions based on

at $\gamma_{C=O}$ 1,890 cm$^{-1}$ and 1,877 cm$^{-1}$.

EXAMPLE 2

The procedure of Example 1 was repeated, except that 40.5 g of methyl 3-diethylamino-iso-butyrate was used as a raw material and 278 A.hr electrolysis was carried out until the electrolytic voltage initially set in the range of 6.1 to 6.4 V reached 6.7 V.

After the electrolysis, the drain cock at the lower end of the electrolytic cell was opened to remove 39.9 g of fluorocarbon mixture. In the cooled trap, 17.6 g of a fluorocarbon mixture was collected. These products were treated and analyzed in the same manner as in Example 1 at it was found that the treatment produced 32.3 g of perfluoro(3-diethylamino-iso-butyryl fluoride) (yield 29.6%). In this case, the treatment simultanously produced perfluoro(iso-butyryl fluoride) and perfluoro(N,N-diethyl-n-propylamine) as cleavage compounds.

The perfluoro(3-diethylamino-iso-butyryl fluoride) mentioned above is a novel compound, possessing a boiling point of 105° to 107° C., a $n_D^{20}$ value of 1.2880, and a $d_4^{20}$ value of 1.8022 and, in the infrared absorption spectrum, exhibiting characteristic absorptions based on

at $\gamma_{C=O}$ 1,893 cm$^{-1}$ and 1,877 cm$^{-1}$.

EXAMPLE 3

The procedure of Example 1 was repeated, except that 40.4 g of methyl 3-pyrrolidino-iso-butyrate was used as a raw material and 234 A.hr electrolysis was carried out until the electrolytic voltage initially set in the range of 6.5 to 6.6 V reached 7.3 V. After the electrolysis, the drain cock at the lower end of the electrolytic cell was opened to obtain 50.8 g of a fluorocarbon mixture. In the cooled trap, 9.0 g of a fluorocarbon mixture was obtained. When these products were treated and analyzed, it was found that the treatment produced 40.1 g of perfluoro(3-pyrrolidino-iso-butyryl fluoride) (yield 43.3%). In this case, the treatment simultaneously produced perfluoro-(iso-butyryl fluoride) and perfluoro(n-propylpyrrolidine) as cleavage compounds.

The perfluoro(3-pyrrolidino-iso-butyryl fluoride) is a novel compound, possessing a boiling point in the range of 105° to 106° C., a $n_D^{20}$ value of 1.2943, and a $d_4^{20}$ value of 1.7833 and, in the infrared absorption spectrum, exhibiting characteristic absorption based on

at $\gamma_{C=O}$ 1,890 cm$^{-1}$ and 1,874 cm$^{-1}$.

EXAMPLE 4

The procedure of Example 1 was repeated, except that 39.8 g of methyl 3-morpholino-iso-butyrate was used as a raw material and 252 A.hr electrolysis was carried out until the electrolytic voltage initially set in the range of 6.1 to 6.3 V reached 7.3 V. After the electrolysis, the drain cock at the lower end of the electrolytic cell was opened to obtain 57.7 g of a fluorocarbon mixture. In the cooled trap, 8.2 g of a fluorocarbon mixture was collected. When these products were treated and analyzed in the same manner as in Example 1, it was found that the treatment produced 50.9 g of perfluoro(3-morpholino-iso-butyryl fluoride) (yield 55.0%). In this case, the treatment simultaneously produced perfluoro-(iso-butyryl fluoride) and perfluoro(n-propylmorpholine) as cleavage products.

The perfluoro(3-morpholino-iso-butyryl fluoride) is a novel compound, possessing a boiling point in the range of 113° to 114° C., a $n_D^{20}$ value of 1.2969, and a $d_4^{20}$ value of 1.8021 and, in the infrared absorption spectrum, exhibiting characteristic absorptions based on

at $\gamma_{C=O}$ 1,890 cm$^{-1}$ and 1,875 cm$^{-1}$.

EXAMPLE 5

The procedure of Example 1 was repeated, except that 40.4 g of methyl 3-piperidino-iso-butyrate was used as a raw material and 247 A.hr of electrolysis was carried out until the electrolytic voltage set initially in the range of 5.4 to 5.6 V reached 6.4 V. As products of the fluorination, 53.0 g of cell drain compound and 7.2 g of cooled trap condensate were obtained both in the form of fluorocarbon mixture. When they were treated and analyzed in the same manner as in Example 1, it was found that the treatment produced 40.6 g of perfluoro(3-piperidino-iso-butyryl fluoride) (yield 40.4%) in combination with perfluoro(n-propylpipedirine) as a cleavage product.

The perfluoro(3-piperidino-iso-butyryl fluoride) is a novel compound, possessing a boiling point in the range of 121° to 123° C., a $n_D^{20}$ value of 1.2957, and a $d_4^{20}$ value of 1.8270 and exhibiting, in the infrared absorptions spectrum, characteristic absorptions based on

at $\gamma_{C=O}$ 1,890 cm$^{-1}$ and 1,875 cm$^{-1}$.

EXAMPLE 6

The procedure of Example 1 was repeated, except that 40.3 g of methyl 3-(N-methylpiperadino)-iso-butyrate was used as a raw material and 241 A.hr of electrolysis was carried out until the electrolytic voltage set initially in the range of 6.5 to 6.7 V reached 7.6 V. As products of the fluorination, 44.5 g of cell drain compound and 13.3 g of cooled trap condensate were obtained both in the form of fluorocarbon mixture. When they were treated and analyzed in the same manner as in Example 1, it was found that the treatment produced 22.7 g of perfluoro[3-(N-methylpiperadino)-iso-butyryl fluoride] (yield 22.7%) in combination with perfluoro(N'-methyl-N-n-propylpiperadine) and perfluoro[3-(N,N-diethylamino)-iso-butyryl fluoride] obtained as a cleavage compounds.

The perfluoro[3-(N-methylpiperadino)-iso-butyryl fluoride] is a novel compound, exhibiting a boiling point in the range of 167° to 170° C., a $n_D^{20}$ value of 1.3180, and a $d_4^{20}$ value of 1.8838 and exhibiting, in the infrared absorption spectrum characteristic absorptions based on

at $\gamma_{C=O}$ 1,887 cm$^{-1}$ and 1,873 cm$^{-1}$.

EXAMPLE 7

The procedure of Example 1 was repeated, except that 40.9 g of methyl 3-(N,N-dimethylamino)-n-butyrate was used as a raw material and 263 A.hr of electrolysis was carried out until the electrolytic voltage set initially in the range of 6.1 to 6.2 V reached 7.1 V. As products of the fluorination, 18.7 g of cell drain compound and 33.6 g of cooled trap condensate were obtained both in the form of fluorocarbon mixture. When they were treated and analyzed in the same manner as in Example 1, it was found that the treatment produced 16.6 g of perfluoro[3-(N,N-dimethylamino)-n-butyryl fluoride] (yield 16.9%). In this case, a small amount of perfluoro[3-(N,N-dimethylamino)oxolan] was simultaneously formed as a product of cyclization.

The perfluoro[3-(N,N-dimethylamino)-n-butyryl fluoride] is a novel compound, the methyl ester of which possesses a boiling point in the range of 125° to 126° C., a $n_D^{20}$ value of 1.3067, and a $n_D^{20}$ value of 1.6843 and exhibiting, in the infrared absorption spectrum a characteristic absorption based on

at $\gamma_{C=O}$ 1,788 cm$^{-1}$.

EXAMPLE 8

The procedure of Example 1 was repeated, except that 40.6 g of methyl 3(diethylamino)-n-butyrate was used as a raw material and 249 A.hr of electrolysis was carried out until the electrolytic voltage set initially in the range of 6.6 to 6.7 V reached 8.4 V. After the electrolysis, the drain cock at the lower end of the electrolytic cell was opened to obtain 23.6 g of a fluorocarbon mixture. In the cooled trap, 24.8 g of a fluorocarbon mixture was collected. When mixtures were treated and analyzed in the same manner as in Example 1, it was found that the treatment produced 5.2 g of perfluoro(3-diethylamino-n-butyryl fluoride) (yield 4.7%).

The perfluoro(3-diethylamino-n-butyryl fluoride) is a novel compound, the methyl ester of which possesses a boiling point in the range of 159° to 160° C., a $n_D^{20}$ value of 1.3142, and a $d_4^{20}$ value of 1.7508 and in the infrared absorption spectrum, exhibits a characteristic absorption based on

at $\gamma_{C=O}$ 1,788 cm$^{-1}$.

EXAMPLE 9

The procedure of Example 1 was repeated, except that 40.3 g of methyl 3-(pyrrolidino)-n-butyrate was used as a raw material and 221 A.hr of electrolysis was carried out until the electrolytic voltage set initially in the range of 6.4 to 6.5 V reached 7.0 V. After the electrolysis, 45.1 g of cell drain compound and 13.0 g of cooled trap condensate both in the form of fluorocarbon mixture were obtained. When they were treated and analyzed in the same manner as in Example 1, it was found that the treatment produced perfluoro(3-pyrrolidino-n-butyryl fluoride) (yield 21.2%). In this case, a small amount of perfluoro(3-pyrrolidino-oxolane) was produced simultaneously as a product of cyclization.

The perfluoro(3-pyrrolidino-n-butyryl fluoride) is a novel compound, the methyl ester of which possesses a boiling point in the range of 151° to 153° C., a $n_D^{20}$ value of 1.3220, and a $d_4^{20}$ value of 1.7444 and exhibiting in the infrared absorption spectrum a characteristic absorption based on

at $\gamma_{C=O}$ 1,788 cm$^{-1}$.

EXAMPLE 10

The procedure of Example 1 was repeated, except that 40.7 g of methyl 3-(morpholino)-n-butyrate was used as a raw material and 228 A.hr of electrolysis was carried out until the electrolytic voltage set initially in the range of 5.9 to 6.1 V reached 7.0 V. This electrolysis produced 34.1 g of cell drain compound and 12.6 g of cooled trap condensate both in the form of fluorocarbon mixture. When they were treated and analyzed in the same manner as in Example 1, it was found that the treatment produced 12.6 g of perfluoro(3-morpholino-n-butyryl fluoride) (yield 13.5%). In this case, the electrolysis also gave rise to a small amount of perfluoro(3-morpholino-oxolane) as a product of cyclization.

The perfluoro(3-morpholino-n-butyryl fluoride) is a novel compound the methyl ester of which possesses a boiling point in the range of 160° to 163° C., a $n_D^{20}$ value of 1.3248, and a $d_4^{20}$ value of 1.7671 and, in the infrared absorption spectrum, exhibits a characteristic absorption based on

$\gamma_{C=O}$ 1,793 cm$^{-1}$.

EXAMPLE 11

The procedure of Example 1 was repeated, except that 40.3 g of methyl 3-(piperidino)-n-butyrate was used as a raw material and 243 A.hr of electrolysis was carried out until the electrolytic voltage set initially in the range of 6.1 to 6.3 V reached 6.5 V. This electrolysis produced 50.8 g of cell drain compound and 8.6 g of cooled trap condensate both in the form of fluorocarbon mixture. When they were treated and analyzed, it was found that the treatment produced 21.1 g of perfluoro(3-piperidino-n-butyryl fluoride) (yield 21.0%). In this case, a small amount of perfluoro(3-piperidinooxolane) was simultaneously formed as a product of cyclization.

The perfluoro(3-piperidino-n-butyryl fluoride) is a novel compound, the methyl ester of which possesses a boiling point in the range of 167° to 168° C., a $n_D^{20}$ value of 1.3271, and a $d_4^{20}$ value of 1.7958 and, in the infrared absorption spectrum, exhibits a characteristic absorption based on

at $\gamma_{C=O}$ 1,788 cm$^{-1}$.

EXAMPLE 12

The procedure of Example 1 was repeated, except that 40.5 g of methyl 3-(hexamethyleneimino)-n-butyrate was used as a raw material and 243 A.hr of electrolysis was carried out until the electrolytic voltage set initially in the range of 6.5 to 6.6 V reached 8.0 V. This electrolysis produced 55.2 g of cell drain compound and 8.2 g of cooled trap condensate both in the form of fluorocarbon mixture. When they were treated and analyzed in the same manner as in Example 1, it was found that the treatment produced 12.9 g of perfluoro(3-hexamethyleneimino-n-butyryl fluoride) (yield 12.4%) in conjunction with 15.3 g of perfluoro[3-(methylpiperidino)-n-butyryl fluoride] as a product of cyclic isomerization (yield 14.7%).

The perfluoro(3-hexamethyleneimino-n-butyryl fluoride) is a novel compound, the methyl ester of which possesses a boiling point in the range of 186° to 188° C., a $n_D^{20}$ value of 1.3332, and a $d_4^{20}$ value of 1.8162 and, in the infrared absorption spectrum, exhibits a characteristic absorption based on

at $\gamma_{C=O}$ 1,791 cm$^{-1}$.

EXAMPLE 13

The product obtained by subjecting methyl 3-dimethylamino-n-butyrate as a raw material to electrolytic fluorination was distilled to expel the greater part of low boiling compounds and obtain a crude product. The content of perfluoro(3-dimethylamino-n-butyryl fluoride) in the crude product was 33.7% by weight.

First, 30 ml of cold water was placed in a three-neck flask having an inner volume of 200 ml and provided with a reflux condenser and a dropping funnel. While the water was kept cooled with ice water and stirred, 26.0 g of the aforementioned crude product [containing 8.76 g of perfluoro(3-dimethylamino-n-butyryl fluoride)] was gradually added dropwise thereto. The stirring of the contents of the flask was continued for about one hour after completion of the dropwise addition of the crude product. Then, the contents of the flask and phenolphthalein added as an indicator thereto were kept stirred and cooled with ice water and an aqueous concentrated potassium hydroxide solution was added dropwise for neutralization until the resultant mixture showed alkalinity.

Then, the contents of the flask were transferred into a beaker having an inner volume of 300 ml, heated on a hot plate until the greater part of the water contained therein was vaporized. Then, the residue of the vaporization was transferred into a flask having an inner volume of 100 ml and vacuum dried for 16 hours.

The yellow solid substance which remained in the flask after the vacuum drying was comminuted. With a gas inlet tube connected to the top of the flask and helium gas supplied to the flask through the tube at the rate of 100 ml/min, the flask was heated on an oil bath to elevate the temperature from 155° to 200° C. over a period of 18 minutes and further heated from 200° to 250° C. over a period of 45 minutes to effect thermal decomposition of the solid substance. The product of the thermal decomposition was condensed and collected in a trap kept cooled at −78° C. Thus, 7.0 g of fluorocarbon was collected.

On analysis by gas chromatography [liquid phase: 1,6-bis(1,1,12-trihydroperfluorododecyloxy)hexane, carrier: Chromosorb PAW 60 to 80 mesh, carrier: helium], IR, $^{19}$F NMR, and mass, the fluorocarbon was found to contain 0.84 g of perfluoro(N,N-dimethylvinylamine) and 3.73 g of perfluoro(2-dimethylaminopropene). The yield of the perfluoro(2-dimethylaminopropene) was 52.5%. The perfluoro(2-dimethylaminopropene) is a colorless transparent liquid possessing a boiling point in the range of 34° to 36° C. The spectrometric data of this compound are as follows.

$^{19}$F NMR data

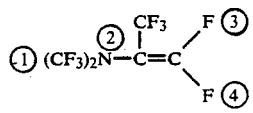

Chemical shift (ppm; based on CFCl$_3$)
① −58.5
② −65.8
③ −72.5
④ −71.3
Coupling constant (Hz)

① − ② = 18.1    ③ − ④ = 15.2

Mass analysis data
m/z
283 M+
264 [M−F]+
195 C$_4$F$_7$N+
Infrared absorption spectrum data
1,749 cm$^{-1}$ (>C=C<)

EXAMPLE 14

A tube of stainless steel measuring 48.0 cm in length and 2.5 cm in inside diameter and provided on the inlet side with an instant vaporizer and a diluting gas flow volume regulating device and on the outlet side with a low-temperature trap for condensation and collection of reaction product was used as a horizontal installation type thermal decomposition reactor.

In this reactor, 86.3 g of powdered sodium carbonate was placed in such a manner that the horizontal level of the packed powder fell roughly halfway along the vertical inner diameter of the tube reactor, with metal wool packed at the opposite inner ends of the tube. The interior of the reactor, with helium passed therethrough at a flow rate of 100 ml/min, was kept at 300° C. for about two hours to dry the sodium carbonate.

As a raw material, the product obtained (as cell drain compound) by subjecting methyl 3-pyrrolidino-n-butyrate to electrolyzing fluorination was used in the unmodified form. This product contained 30.7% by weight of perfluoro(3-pyrrolidino-n-butyryl fluoride).

First, in the reactor which was kept at 220° C., with helium gas kept passed therethrough at a rate of 100 ml/min, 6.91 g of the fluorocarbon mixture mentioned above {containing 2.12 g of perfluoro(3-pyrrolidino-n-butyryl fluoride)} was supplied with a microproportioning pump over a period of 34 minutes to the instantaneous vaporizer. Then, the vaporized fluorocarbon mixture was mixed with helium gas introduced at a fixed rate and the resultant mixture was introduced into the reactor. The reaction product was condensed and collected in the trap kept cooled to −78° C. Consequently, 4.33 g of fluorocarbon mixture was obtained.

When this fluorocarbon mixture was analyzed in the same manner as in Example 13, it was found to contain 1.33 g of perfluoro(2-pyrrolidinopropene) (yield 87.4%). The conversion was 100%. The physical constants of the perfluoro(2-pyrrolidinopropene) are shown in the table.

EXAMPLE 15

The procedure of Example 14 was repeated, except that the product obtained (as cell drain compound) by subjecting methyl 3-morpholino-n-butyrate to electrolytic fluorination was used as a raw material.

The product mentioned above contained 36.8% by weight of perfluoro(3-morpholino-n-butyryl fluoride).

When 5.94 g of the fluorocarbon mixture {containing 2.19 g of perfluoro(3-morpholino-n-butyryl fluoride)} was supplied over a period of 30 minutes to the reactor to be thermally decomposed therein, 4.05 g of fluorocarbon was obtained in the cooled trap.

When this fluorocarbon was analyzed in the same manner as in Example 13, it was found to contain 1.21 g of perfluoro(2-morpholinopropene) (yield 65.3%). The conversion rate was 100%. The physical constants of the perfluoro(2-morpholinopropene) are shown in the table.

EXAMPLE 16

The procedure of Example 14 was repeated, except that the product obtained (as cell drain compound) by subjecting methyl 3-piperidino-n-butyrate to electrolytic fluorination was used as a raw material.

This product contained 41.5% by weight of perfluoro(3-piperidino-n-butyryl fluoride).

When 5.37 g of the fluorocarbon mixture {containing 2.23 g of perfluoro(3-piperidino-n-butyryl fluoride)} was supplied over a period of 30 minutes to the reactor and thermally decomposed therein, 3.17 g of fluorocarbon was obtained in the cooled trap.

When this fluorocarbon was analyzed in the same manner as in Example 13, 1.05 g of perfluoro(2-piperidinopropene) was obtained (yield 55.1%). The physical constants of the perfluoro(2-piperidinopropane) are shown in the table.

EXAMPLE 17

The procedure of Example 13 was repeated, except that the product obtained (as cell drain compound) by subjecting methyl 3-hexamethyleneimino-n-butyrate to electrolytic fluorination was used as a raw material. This product contained 27.7% by weight of perfluoro[3-(methylpiperidino)-n-butyryl fluoride] and 23.4% by weight of perfluoro(3-hexamethyleneimino-n-butyryl fluoride).

By treating 26.0 g of the fluorocarbon mixture {containing 7.20 g of perfluoro[3-(methylpiperidino)-n-butyryl fluoride] and 6.10 g of perfluoro(3-hexamethyleneimino-n-butyryl fluoride)} in the same manner as in Example 13, 17.10 g of dry light yellow solid substance was obtained.

The thermal decomposition reaction was carried out under a vacuum (3 mmHg). To be specific, the light yellow solid substance in a finely comminuted form was placed in a flask having an inner volume of 200 ml. With a trap connected to the flask, the interior of the flask was vacuumized to 3 mmHg by a vacuum pump. Then, the flask was placed on an oil bath, heated from 150° to 200° C. over a period of 13 minutes, and further heated to 220° C. over a period of 15 minutes, to effect thermal decomposition of the contents thereof. As a result, 9.48 g of fluorocarbon was collected in a trap cooled to −78° C.

When the fluorocarbon was analyzed in the same manner as in Example 13, it was found that the thermal decomposition produced 3.73 g of perfluoro[2-(methylpiperidino)propene] (yield 59.5%) and 6.23 g of perfluoro(2-hexamethyleneiminopropene) (yield 52.2%). The physical constants of the perfluoro(2-hexamethyleneiminopropene) are shown in the table.

| | | | | $^{19}$F NMR | |
|---|---|---|---|---|---|
| Example | Perfluoro(2-dialkylamino-propene) | B.P. (°C.) | IR(cm$^{-1}$) (C=C) | Chemical shift (ppm; based on CFCl$_3$) | (Hz) |
| 14 | 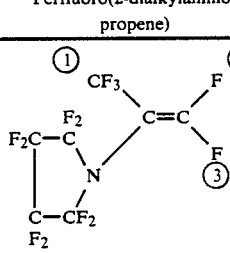 | 77.5~80.0 | 1745 | ①  - 63.8<br>②  - 67.7<br>③  - 68.7 | ①-② = 18.1<br>②-③ = 19.8 |

-continued

| Example | Perfluoro(2-dialkylamino-propene) | B.P. (°C.) | IR(cm$^{-1}$) (C=C) | $^{19}$F NMR Chemical shift (ppm; based on CFCl$_3$) | (Hz) |
|---|---|---|---|---|---|
| 15 | ①CF$_3$, ②F, C=C, N-③F, ring: F$_2$C-CF$_2$-O-CF$_2$-CF$_2$ | 89.5~91.5 | 1744 | ① -64.3<br>② -69.6<br>③ -68.9 | ①-② = 17.5 |
| 16 | ①CF$_3$, ②F, C=C, N-③F, ring: F$_2$C-CF$_2$-CF$_2$-CF$_2$-CF$_2$ | 103.5~104.5 | 1745 | ① -64.9<br>② -69.6<br>③ -68.8 | ①-② = 19.8<br>②-③ = 15.8 |
| 17 | ①CF$_3$, ②F, C=C, N-③F, ring: F$_2$C-CF$_2$-CF$_2$-CF$_2$-C-C-F$_2$F$_2$ | 125.5~126.0 | 1747 | ① -63.7<br>② -70.2<br>③ -68.7 | ①-② = 15.8<br>②-③ = 14.7 |

EXAMPLE 18

The procedure of Example 14 was repeated, except that the product obtained (as cell drain compound) by subjecting methyl 3-dimethyleneamino-iso-butyrate to electrolytic fluorination was used as a raw material.

This product contained 84.4% by weight of perfluoro(3-dimethylamino-iso-butyryl fluoride) and 7.8% by weight of perfluoro(methyl 3-dimethylamino-iso-butyrate).

When 5.03 g of the fluorocarbon mixture mentioned above containing 4.24 g of perfluoro(3-dimethylamino-iso-butyryl fluoride) and 0.39 g of perfluoro(methyl 3-dimethylamino-iso-butyrate) was supplied to the reactor over a period of 40 minutes and thermally decomposed therein, 2.67 g of fluorocarbon was obtained in the cooled trap. When this fluorocarbon was analyzed in the same manner as in Example 13, it was found to contain 0.50 g of trans-form perfluoro(3-dimethylamino-2-propene) (boiling point 30° to 32° C.) (yield 13.5%), 1.38 g of cis-form perfluoro(3-dimethylamino-2-propene) (boiling point 33° to 34° C.) (yield 37.3%), and 0.35 g of perfluoro(3-dimethylamino-1-propene) (boiling point 42° to 43° C.) (yield 9.5%). In this case, the conversion was 100%. The spectral data of these components are shown below.

o Trans-perfluoro(3-dimethylamino-2-propene):
$^{19}$F NMR data

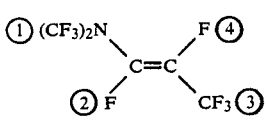

Chemical shift (ppm; based on CFCl$_3$)
① −57.6 (d, d)
② −113.4 (d, q)
③ −69.3 (d, d)
④ −156.2 (d)

①  − ② = 3.7,  ① − ④ = 3.7,
② − ③ = 22.3, ② − ④ = 135,
① − ④ = 9.9

Mass analysis data
m/z
283 M$^+$
264 [M−F]$^+$
245 C$_5$F$_9$N$^+$
Infrared absorption spectrum data
1,756 cm$^{-1}$ (>C=C<)

o Cis-perfluoro(3-dimethylamino-2-propene):
$^{19}$F NMR data

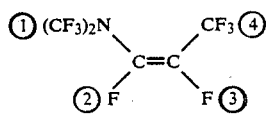

Chemical shift (ppm; based on CFCl$_3$)
① −57.5 (m)
② −97.7 (m)
③ −142.1 (q, d)
④ −69.0 (t, kept)
Coupling constant (Hz)

② − ③ = 20.6, ② − ④ = 10.4,
③ − ④ = 10.6, ④ − ① = 2

Mass analysis data
m/z
283 M+
264 [M−F]+
195 C₄F₇N+
Infrared absorption spectrum data
1,759 cm⁻¹ (>C=C<)
o Perfluoro(3-dimethylamino-1-propene):
¹⁹F NMR data

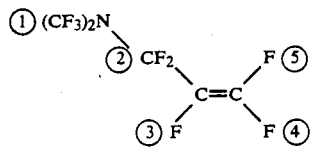

Chemical shift (ppm; based on CFCl₃)
① −53.9 (t)
② −81.0 (m)
③ −186.2 (d, d, t)
④ −92.2 (d, d, t)
⑤ −104.6 (d, d, t)
Coupling constant (Hz)

① − ③ = 12.0, ① − ⑤ = 12.0,
② − ③ = 15.8, ② − ④ = 7.4,
② − ⑤ = 28.3, ③ − ④ = 40.7,
③ − ⑤ = 118.7, ④ − ⑤ = 54.2

Mass analysis data
m/z
283 M+
264 [M−F]+
202 C₃F₈N+
Infrared absorption spectrum data
1,791 cm⁻¹ (>C=C<)

EXAMPLE 19

In a flask having an inner volume of 50 ml and provided with a reflux condenser, 6.16 g of methyl ester of perfluoro(3-dimethylamino-iso-butyric acid), 20 ml of methanol, 1.20 g of potassium hydroxide, and 1 ml of water were magnetically stirred and held at room temperature for 20 hours to be saponified. The reaction mixture was deprived of the greater part of methanol by means of a rotary evaporator and then vacuum dried at room temperature for four hours. As a result, 4.11 g of a white solid substance was obtained in the flask.

The thermal decomposition of this white solid substance was carried out on an oil bath under a vacuum (3 torrs) by elevating the temperature from 140° to 200° C. over a period of about 25 minutes and further from 200° to 240° C. over a period of 30 minutes. The product was condensed and collected in a trap cooled with liquefied nitrogen. First, the cooled trap containing the crude product was immersed in an ethanol/dry ice bath and suctioned under a vacuum (3 torrs) for several minutes for expulsion of the entrained carbon dioxide gas. The product consequently obtained weighed 2.18 g. When this product was analyzed in the same manner as in Example 13, it was found to contain 0.46 g of trans-perfluoro(3-dimethylamino-2-propene) (yield 11.2%), 1.36 g of cis-perfluoro(3-dimethylamino-2-propene) (yield 33.2%), and 0.32 g of perfluoro(3-dimethylamino-1-propene) (yield 7.7%).

EXAMPLE 20

The procedure of Example 14 was repeated, except that the product methyl 3-diethylamino-iso-butyrate to electrolytic fluorination was used as a raw material. This compound contained 79.4% by weight of perfluoro(3-diethylamino-iso-butyryl fluoride). When 6.71 g of the fluorocarbon mixture [containing 5.33 g of perfluoro(3-diethylamino-iso-butyryl fluoride)] was supplied over a period of 30 minutes to the reactor and thermally decomposed therein, 4.43 g of fluorocarbon was obtained in the cooled trap.

When the fluorocarbon was analyzed in the same manner as in Example 13, it was found to contain 0.99 g of trans-perfluoro(3-diethylamino-2-propene) (boiling point 74.0° to 74.5° C.) (yield 23.2%), 3.47 g of cis-perfluoro(3-diethylamino-2-propene) (boiling point 77.5° to 78.5° C.) (yield 31.0%), 1.00 g of perfluoro(3-diethylamino-1-propene) (boiling point 85.5° to 86.5° C.) (yield 23.3%), and 0.14 g of perfluoro(N,N-diethylvinylamine). In this case, the conversion was 90.2%.

EXAMPLE 21

The procedure of Example 14 was repeated, except that the product obtained (as cell drain compound) by subjecting methyl 3-pyrrolidino-iso-butyrate to electrolytic fluorination was used as a raw material. This product contained 83.7% by weight of perfluoro(3-pyrrolidino-iso-butyryl fluoride).

When 6.95 g of the fluorocarbon mixture [containing 6.07 g of perfluoro(3-pyrrolidino-iso-butyryl fluoride)] was supplied over a period of 30 minutes to the reactor and thermally decomposed therein, 4.64 g of fluorocarbon was obtain in the cooled trap.

When the fluorocarbon was analyzed in the same manner as in Example 13, it was found to contain 4.06 g of trans-perfluoro(3-pyrrolidino-2-propene) (boiling point 75.5° to 76.5° C.) (yield 27.5%), 5.07 g of cis-perfluoro(3-pyrrolidino-2-propene) (boiling point 77.0° to 78.0° C.) (yield 34.3%), 2.23 g of perfluoro(3-pyrrolidino-1-propene) (boiling point 78.5° to 80.0° C.) (yield 15.1%), and 0.10 g of perfluoro(N-vinylpyrrolidine). In this case, the conversion rate was 100%.

EXAMPLE 22

The procedure of Example 14 was repeated, except that calcium carbonate (47.7 g) was used as a packing material, the reaction temperature was fixed at 300° C., and the product obtained (as cell drain compound) by subjecting methyl 3-morpholino-iso-butyrate to electrolytic fluorination was used as a raw material. The product contained 84.3% by weight of perfluoro(3-morpholino-iso-butyryl fluoride).

When 8.38 g of the fluorocarbon mixture [containing 7.06 g of perfluoro(3-morpholino-iso-butyryl fluoride)] was supplied over a period of 38 minutes to the reactor and thermally decomposed therein, 5.74 g of fluorocarbon was obtained in the cooled trap.

When this fluorocarbon was analyzed in the same manner as in Example 13, it was found to contain 0.96 g of trans-perfluoro(3-morpholino-2-propene) (boiling point 83.0° to 83.5° C.) (yield 16.1%), 1.96 g of cis-perfluoro(3-morpholino-2-propene) (boiling point 85.5° to 86.5° C.) (yield 32.8%), 1.66 g of perfluoro(3-morpholino-1-propene) (boiling point 89.5° to 91.0° C.)

(yield 27.8%), and 0.31 g of perfluoro(N-vinylmorpholine). In this case, the conversion rate was 100%.

EXAMPLE 23

With the same reaction used in Example 14, the procedure of Example 22 was repeated, except that the product obtained (as cell drain compound) by subjecting methyl 3-piperidino-iso-butyrate to electrolytic fluorination was used as a raw material.

This product contained 76.5% by weight of perfluoro(3-piperidino-iso-butyryl fluoride).

When 6.37 g of the fluorocarbon mixture [containing 4.88 g of perfluoro(3-piperidino-iso-butyryl fluoride)] was supplied over a period of 28 minutes to the reactor and thermally decomposed therein, 4.00 g of fluorocarbon was obtained in the cooled trap.

When this fluorocarbon was analyzed in the same manner as in Example 13, it was found to contain 0.80 g of trans-perfluoro(3-piperidino-2-propene) (boiling point 95.0° to 95.5° C.) (yield 19.2%), 1.87 g of cis-perfluoro(3-piperidino-2-propene) (boiling point 97.5° to 98.5° C.) (yield 44.7%), 0.37 g of perfluoro(3-piperidino-1-propene) (boiling point 107.0° to 108.0° C.) (yield 8.9%), and 0.49 g of perfluoro(N-vinylpiperidine).

EXAMPLE 24

The procedure of Example 14 was repeated, except that the reaction temperature was fixed at 250° C. and perfluoro[3-(N'-methylpiperadino)-iso-butyryl fluoride] purified by gas chromatography was used as a raw material.

When 2.14 g of the perfluoro[3-(N'-methylpiperadino)-iso-butyryl fluoride] was supplied over a period of 9 minutes to the reactor and thermally decomposed therein, 1.30 g of fluorocarbon was obtained in the cooled trap.

When the fluorocarbon was analyzed in the same manner as in Example 13, it was found to contain 0.41 g of trans-perfluoro[3-(N'-methylpiperadino)-2-propene] (boiling point 106.5° to 108.5° C.) (yield 21.9%), 0.68 g of cis-perfluoro[3-(N'-methylpiperadino)-2-propene] (boiling point 110.5° to 111.5° C.) (yield 36.7%), and 0.50 g of perfluoro[3-(N'-methylpiperadino)-1-propene] (boiling point 116.5° to 117.5° C.) (yield 11.6%).

What is claimed is:

1. A perfluoro(dialkylaminopropene) represented by the formula A"-B", wherein A" stands for

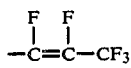

and B" for a perfluoro-di-substituted amino group having a total of 4 to 6 backbone carbon atoms and represented by the formula

wherein $R_1$ and $R_2$ independently stand for a perfluoroalkyl group of 1 to 5 carbon atoms and may be bonded directly to each other or indirectly through the medium of an oxygen atom or a nitrogen atom.

2. The perfluoro(dialkylaminopropene) according to claim 1, wherein B" is

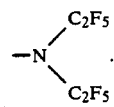

3. The perfluoro(dialkylaminopropene) according to claim 1, wherein B" is

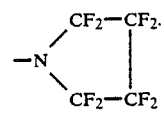

4. The perfluoro(dialkylaminopropene) according to claim 1, wherein B" is

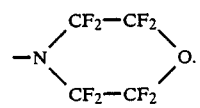

5. The perfluoro(dialkylaminopropene) according to claim 1, wherein B" is

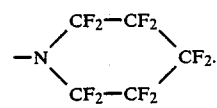

6. The perfluoro(dialkylaminopropene) according to claim 1, wherein B" is

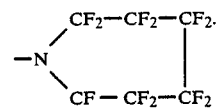

7. A perfluoro(dialkylaminopropene) represented by the formula A"-B", wherein A" stands for

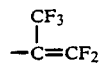

and B" for a perfluoro-di-substituted amino group having a total of 2 to 6 backbone carbon atoms and represented by the formula

wherein $R_1$ and $R_2$ independently stand for a perfluoroalkyl group of 1 to 5 carbon atoms and may be bonded directly to each other or indirectly through the medium of an oxygen atom or a nitrogen atom.

8. The perfluoro(dialkylaminopropene) according to claim 7, wherein B" is

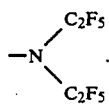
9. The perfluoro(dialkylaminopropene) according to claim 7, wherein B″ is
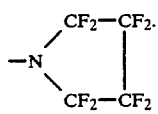
10. The perfluoro(dialkylaminopropene) according to claim 7, wherein B″ is
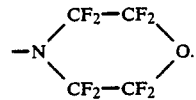
11. The perfluoro(dialkylaminopropene) according to claim 7, wherein B″ is
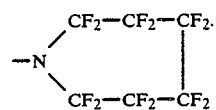
12. The perfluoro(dialkylaminopropene) according to claim 7, wherein B″ is
* * * * *